United States Patent
Heider et al.

(10) Patent No.: US 6,719,838 B2
(45) Date of Patent: Apr. 13, 2004

(54) COLORED INTERFERENCE PIGMENTS

(75) Inventors: Lilia Heider, Riedstadt (DE); Manuela Loch, Merxheim (DE); Nicole Schupp, Gross-Bieberau (DE); Helge Kniess, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/279,017

(22) Filed: Oct. 24, 2002

(65) Prior Publication Data
US 2003/0097965 A1 May 29, 2003

(30) Foreign Application Priority Data
Oct. 24, 2001 (DE) .......................... 101 51 844

(51) Int. Cl.[7] .............................. C04B 14/20
(52) U.S. Cl. ................ 106/417; 106/415; 106/436; 106/439; 106/440; 106/479; 106/481
(58) Field of Search ................. 106/415, 417, 106/436, 439, 440, 479, 481

(56) References Cited

U.S. PATENT DOCUMENTS

| 4,344,987 A | 8/1982 | Ostertag et al. |
| 4,482,389 A | 11/1984 | Franz et al. |
| 4,494,993 A | 1/1985 | Bernhard et al. |
| 4,544,415 A | 10/1985 | Franz et al. |
| 4,552,593 A | 11/1985 | Ostertag |
| 4,948,631 A | 8/1990 | Ostertag et al. |
| 5,332,767 A | 7/1994 | Reisser et al. |
| 5,759,255 A | 6/1998 | Venturini et al. |
| 5,958,125 A | 9/1999 | Schmid et al. |
| 6,139,614 A * | 10/2000 | Schmid et al. ............... 106/417 |

FOREIGN PATENT DOCUMENTS

| EP | 0 649 886 | 4/1995 |
| WO | WO 97/29059 | 8/1997 |
| WO | WO 99/57204 | 11/1999 |

* cited by examiner

Primary Examiner—C. Melissa Koslow
Assistant Examiner—Shalie A. Manlove
(74) Attorney, Agent, or Firm—Millen, White, Zelano, Branigan, P.C.

(57) ABSTRACT

The present invention relates to colored interference pigments based on multicoated, platelet-shaped substrates, which are distinguished in that they comprise
(A) a colored coating having a refractive index of $n > 1.8$,
(B) a colorless coating having a refractive index of $n > 1.8$,
(C) a colorless coating having a refractive index of $n \leq 1.8$,
(D) a colorless coating having a refractive index of $n > 1.8$, and optionally
(E) an outer protective layer,
and to their use in paints, surface coatings, printing inks, plastics, ceramic materials, glasses, for laser marking, in cosmetic formulations and for the production of pigment preparations and dry preparations.

34 Claims, No Drawings

COLORED INTERFERENCE PIGMENTS

The present invention relates to coloured interference pigments based on multicoated platelet-shaped substrates.

Lustre or effect pigments are employed in many areas of industry, in particular in the area of automotive paints, decorative coatings, plastics, surface coatings, printing inks and cosmetic formulations.

Lustre pigments based on transparent platelet-shaped substrates which do not have a "hard" metallic lustre are the subject-matter of WO 93/12182. Mica platelets are covered with a high-refractive-index metal-oxide layer, such as, for example, $TiO_2$, and a non-selectively absorbing layer. Depending on the $TiO_2$ layer thickness, these pigments exhibit a certain interference colour when viewed perpendicularly which becomes weaker and weaker with increasingly oblique viewing angle and finally drops off to grey or black. The interference colour does not change, but a decrease in colour saturation is observed.

EP 0 753 545 A2 discloses goniochromatic lustre pigments based on multicoated, high-refractive-index, non-metallic, platelet-shaped substrates which are at least partially transparent to visible light, which pigments have at least one layer pack comprising a colourless, low-refractive-index coating and a reflective coating which absorbs selectively or non-selectively.

The multilayer pigments known from the prior art are in some cases built up from layer materials which have little or no transparency to light and can therefore only be combined with absorption pigments in a very restricted manner in use. In addition, the interference colour of these pigments is highly dependent on the viewing angle, which is undesired in the majority of applications. Furthermore, these pigments are in some cases very difficult to prepare or reproduce.

An object of the present invention is to provide coloured multilayer pigments of high tinting strength which do not have pronounced goniochromaticity, are distinguished by their advantageous applicational properties and at the same time can be prepared in a simple manner.

Upon further study of the specification and appended claims, further objects and advantages of this invention will become apparent to those skilled in the art.

Surprisingly, coloured interference pigments based on multicoated, platelet-shaped substrates have now been found on which firstly a defined absorption is produced and subsequently an interference system is defined. This combination of absorption and interference on a platelet-shaped substrate results in a coloured pigment having high colour purity of the interference colour and intense lustre.

The pigments according to the invention are distinguished over the pigments from the prior art through their extraordinarily high chroma C, their high hiding power, their high colour purity of the interference colour and high brightness. In contrast to the goniochromatic pigments from the prior art, they do not exhibit any angle dependence of the interference colour.

The invention thus relates to coloured interference pigments based on multicoated, platelet-shaped substrates, characterised in that they comprise (A) a coloured coating having a refractive index of n>1.8,
(B) a colourless coating having a refractive index of n>1.8,
(C) a colourless coating having a refractive index of n≦1.8,
(D) a colourless coating having a refractive index of n>1.8, and optionally
(E) an outer protective layer.

The invention furthermore relates to the use of the interference pigments according to the invention in paints, coatings, printing inks, plastics, ceramic materials, glasses and for laser marking. Owing to the high colour strength, the pigments according to the invention are particularly suitable for decorative cosmetics. Furthermore, the pigments according to the invention are also suitable for the production of pigment preparations and for the production of dry preparations, such as, for example, granules, chips, pellets, briquettes, etc. The dry preparations are particularly suitable for printing inks, coatings and cosmetic formulations.

Suitable base substrates for the coloured pigments according to the invention are transparent platelet-shaped substrates. Preferred substrates are phyllosilicates. Particularly suitable substrates are natural or synthetic mica, talc, kaolin, platelet-shaped iron oxides or aluminium oxides, BiOCl, glass platelets, $SiO_2$ platelets, $TiO_2$ platelets, graphite platelets, synthetic support-free platelets, or other comparable materials. It is also possible to employ mixtures of different substrates. Particularly preferred substrate mixtures are mica platelets+$SiO_2$ platelets
mica platelets+$Al_2O_3$ platelets
mica platelets+glass platelets
mica platelets+$TiO_2$ platelets
mica platelets+oxynitride platelets
mica platelets+nitride platelets
mica platelets+pearl essence
mica platelets+graphite platelets
mica platelets+BiOCl
$SiO_2$ platelets+$Al_2O_3$ platelets
glass platelets+$SiO_2$ platelets The size of the base substrates is not crucial per se and can be matched to the respective application. In general, the platelet-shaped substrates have a thickness of between 0.05 and 1.5 μm, in particular between 0.1 and 1 μm. The extension in the two other regions is usually between 1 and 250 μm, preferably between 2 and 200 μm, and in particular between 5 and 60 μm. It is also possible to employ substrates having different particle sizes. Particular preference is given to a mixture of mica fractions of N mica (10–60 μm) and F mica (5–20 μm). Preference is furthermore given to N and S fractions (10–130 μm) and F and S fractions (5–130 μm).

The thickness of the individual layers on the base substrate is essential for the optical properties of the pigment. Layer (A) in particular has a significant effect on the colour properties The interference pigments according to the invention have an absorption layer (A) and an interference system (B, C, D), the latter consisting of alternating high-refractive-index layers (B, D) and low-refractive-index layer (C). The high-refractive-index layers (B) and (D) have a refractive index of n>1.8, preferably n≧2.0.

Layer (A) preferably consists of coloured oxides, sulfides, tellurides, selenides or mixed systems of these anions and of the elements from main groups 2–5 and subgroups 1, 2 and 4–8, furthermore the lanthanides and actinides. Layer (A) particularly preferably consists of $Fe_2O_3$, $Fe_3O_4$, $Ce_2O_3$, $Cr_2O_3$, Ti suboxides ($TiO_2$ partially reduced with oxidation states of from <4 to 2 and lower oxides, such as $Ti_3O_5$, $Ti_2O_3$ up to TiO), titanium oxynitrides and titanium nitride, molybdenum oxides, CoO, $Co_3O_4$, $VO_2$, $V_2O_3$, NiO, $MoS_2$, $WS_2$, $V_2O_5$, CuO, $Cu_2O$, $Ag_2O$, $CeO_2$, $MnO_2$, $Mn_2O_3$, $Mn_2O_5$ or mixtures or combinations (mixed oxides) thereof. Layer (A) particularly preferably consists of $Fe_2O_3$, $Fe_3O_4$, furthermore of $Cr_2O_3$, CoO, $Co_3O_4$, $VO_2$, $V_2O_3$, NiO, $MoS_2$, $WS_2$, $V_2O_5$, CuO, $CeO_2$, $Ce_2O_3$, $MnO_2$, $Mn_2O_3$ and/or $Ag_2O$.

Layers (B) and (D) preferably consist of $TiO_2$, $ZrO_2$, $SnO_2$, ZnO or BiOCl. Layers (B) and (D) are particularly preferably a $TiO_2$ layer. The $TiO_2$ here can be in the rutile or anatase modification, preferably rutile.

Materials which are suitable as colourless, low-refractive-index materials for coating (C) are preferably metal oxides or the corresponding oxide hydrates, such as, for example, $SiO_2$, $Al_2O_3$, AlO(OH), $B_2O_3$, $MgF_2$, $MgSiO_3$, or a mixture of the said metal oxides. Layer (C) preferably consists of $SiO_2$, $MgF_2$, $Al_2O_3$ or mixtures thereof.

It is advantageous for the optical properties of the pigments according to the invention if layer (A) is very thin. The thickness of layer (A) is preferably from 1 to 100 nm, in particular from 1 to 50 nm and particularly preferably from 5 to 20 nm.

The thickness of layers (B) and (D) is preferably from 20 to 250 nm, in particular from 25 to 180 nm and particularly preferably from 40 to 150 nm. The layer thicknesses of layers (B) and (D) may be identical or different. They preferably have similar or identical layer thicknesses.

The thickness of layer (C) is preferably from 20 to 200 nm, in particular from 30 to 180 nm and particularly preferably from 40 to 150 nm.

The coating of the substrates with an absorption layer (A) and with a high-refractive-index layer (B), a low-refractive-index layer (C) and a further, colourless, high-refractive-index layer (D) results in the formation of coloured interference pigments whose colour, lustre and hiding power can be varied within broad limits.

Particularly preferred interference pigments have the following layer sequences:
substrate+$Fe_2O_3$ (A)+$TiO_2$ (B)+$SiO_2$ (C)+$TiO_2$ (D)
substrate+$Fe_3O_4$ (A)+$TiO_2$ (B)+$SiO_2$ (C)+$TiO_2$ (D)
substrate+$Fe_2O_3$ (A)+$TiO_2$ (B)+$Al_2O_3$ (C)+$TiO_2$ (D)
substrate+$Fe_3O_4$ (A)+$TiO_2$ (B)+$Al_2O_3$ (C)+$TiO_2$ (D)
substrate+$V_2O_5$ (A)+$TiO_2$ (B)+$SiO_2$ (C)+$TiO_2$ (D)
substrate+$MnO_2$ (A)+$TiO_2$ (B)+$SiO_2$ (C)+$TiO_2$ (D)
substrate+$MnO_2$ (A)+$TiO_2$ (B)+$Al_2O_3$ (C)+$TiO_2$ (D)
substrate+$Ag_2O$ (A)+$TiO_2$ (B)+$SiO_2$ (C)+$TiO_2$ (D)
substrate+$Ag_2O$ (A)+$TiO_2$ (B)+$Al_2O_3$ (C)+$TiO_2$ (D)
substrate+CoO (A)+$TiO_2$ (B)+$SiO_2$ (C)+$TiO_2$ (D)
substrate+$Cr_2O_3$ (A)+$TiO_2$ (B)+$SiO_2$ (C)+$TiO_2$ (D)
substrate+$Cr_2O_3$ (A)+$TiO_2$ (B)+$Al_2O_3$ (C)+$TiO_2$ (D)
substrate+Ti suboxides (A)+$TiO_2$ (B)+$SiO_2$ (C)+$TiO_2$ (D)
substrate+Ti suboxides (A)+$TiO_2$ (B)+$Al_2O_3$ (C)+$TiO_2$ (D)
substrate+$Fe_2O_3$ (A)+$ZrO_2$ (B)+$SiO_2$ (C)+$ZrO_2$ (D)
substrate+$Fe_2O_3$ (A)+ZnO (B)+$SiO_2$ (C)+$ZrO_2$ (D)
substrate+$Fe_3O_4$ (A)+$ZrO_2$ (B)+$SiO_2$ (C)+$ZrO_2$ (D)
substrate+$Fe_3O_4$ (A)+$ZrO_2$ (B)+$SiO_2$ (C)+$TiO_2$ (D)
substrate+$Fe_2O_3$ (A)+$TiO_2$ (B)+$SiO_2$ (C)+$ZrO_2$ (D)

The pigments according to the invention can easily be prepared by the production of an absorption layer and high- and low-refractive-index interference layers with precisely defined thickness and a smooth surface on the finely divided, platelet-shaped substrates.

The metal-oxide layers are preferably applied by wet-chemical methods, it being possible to use the wet-chemical coating methods developed for the production of pearlescent pigments. Methods of this type are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017 or in further patent documents and other publications known to the person skilled in the art.

In the case of wet coating, the substrate particles are suspended in water, and one or more hydrolysable metal salts are added at a pH which is suitable for hydrolysis, the latter being selected in such a way that the metal oxides or metal oxide hydrates are precipitated directly onto the platelets without secondary precipitations occurring. The pH is usually kept constant by simultaneous metering-in of a base or acid. The pigments are subsequently separated off, washed and dried and calcined in a reduced atmosphere, it being possible for the calcination temperature to be optimised with respect to the coating present in each case. In general, the calcination temperatures are between 250 and 900° C., preferably between 450 and 700° C. If desired, the pigments can be separated off, dried or calcined after application of individual coatings and then re-suspended for precipitation of the further layers.

Coating can furthermore also be carried out in a fluidised-bed reactor by gas-phase coating, it being possible, for example, correspondingly to use the processes proposed in EP 0 045 851 and EP 0 106 235 for the production of pearlescent pigments.

The $Fe_3O_4$ layer can be produced, for example, by reduction of the $Fe_3O_4$ layer using ammonia, hydrogen or alternatively hydrocarbons and hydrocarbon/ammonia mixtures, as described, for example, in EP-A-0 332 071, DE 19 51 696.8 and DE 19 51 697.7. The reduction is preferably carried out in a forming gas atmosphere ($N_2/H_2$), in particular with 92% of $N_2$/8% of $H_2$ or 96% of $N_2$/6% of $H_2$. The reduction temperature is preferably from 400 to 700° C., in particular from 500 to 600° C.

The colour shade of the pigments can be varied within broad limits by selecting different covering amounts or layer thicknesses resulting therefrom. The fine tuning for a certain colour shade can be achieved beyond the pure choice of amount by approaching the desired colour under visual or measurement technology control.

In order to increase the light, water and weather stability, it is frequently advisable, depending on the area of application, to subject the finished pigment to post-coating or post-treatment. Suitable post-coatings or post-treatments are, for example, the processes described in German Patent 22 15 191, DE-A 31 51 354, DE-A 32 35 017, DE-A 33 34 598, DE 40 30 727 A1, EP 0 649 886 A2, WO 97/29059, WO 99/57204, U.S. Pat. No. 5,759,255. This post-coating (layer E) further increases the chemical stability of the pigments or simplifies handling of the pigment, in particular incorporation into various media.

The pigments according to the invention are compatible with a large number of colour systems, preferably from the area of paints, coatings and printing inks. For the production of printing inks, a large number of binders, in particular water-soluble grades, is suitable, as marketed, for example, by BASF, Marabu, Pröll, Sericol, Hartmann, Gebr. Schmidt, Sicpa, Aarberg, Siegberg, GSB-Wahl, Follmann, Ruco or Coates Screen INKS GmbH. The printing inks may be water-based or solvent-based. The pigments are furthermore also suitable for the laser marking of paper and plastics, and for applications in the agricultural sector, for example for greenhouse sheeting, and, for example, for the colouring of tent awnings.

It goes without saying that, for the various applications, the multilayer pigments can also advantageously be used in the form of a mixture with organic dyes, organic pigments or other pigments, such as, for example, transparent and hiding white, coloured and black pigments, and with platelet-shaped iron oxides, organic pigments, holographic pigments, LCPs (liquid crystal polymers) and conventional transparent, coloured and black lustre pigments based on metal oxide-coated mica and $SiO_2$ platelets, etc. The multilayer pigments can be mixed with commercially available pigments and fillers in any ratio.

The pigments according to the invention are furthermore suitable for the production of flowable pigment preparations and dry preparations. The pigment preparations and dry preparations are distinguished by the fact that they comprise one or more pigments according to the invention, binders and optionally one or more additives.

The invention thus also relates to the use of the pigments in formulations such as paints, printing inks, coatings, plastics, ceramic materials, glasses, in cosmetic formulations, for laser marking and for the production of pigment preparations and dry preparations.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. DE 101 51 844.7, filed Oct. 24, 2001 is hereby incorporated by reference.

The following examples are intended to explain the invention in greater detail, but without restricting it.

EXAMPLES

Example 1

Mica+Fe$_3$O$_4$+TiO$_2$+SiO$_2$+TiO$_2$ 100 g of mica having a particle size of 10–60 μm are suspended in 1.9 l of deionised water and heated to 80° C. with vigorous stirring. The pH of the mica suspension is set to 2.8 using 10% hydrochloric acid. 111.91 g of FeCl$_3$ solution (37.30 g of FeCl$_3$+74.61 g of H$_2$O) are subsequently metered in, during which the pH is kept constant by means of 32% sodium hydroxide solution. The suspension is subsequently stirred for 15 minutes. 890.40 g of TiCl$_4$ solution (474.88 g of TiCl$_4$+415.52 g of H$_2$O) are metered into this suspension at pH=2.1. The pH is then set to 7.0 using sodium hydroxide solution (32%), and 188.89 g of sodium water-glass solution (62.96 g of sodium water-glass (w$_{SiO2}$=27%)+125.93 g of H$_2$O) are metered in at this pH. During this addition, the pH is kept constant using hydrochloric acid (10%). 445.2 g of TiCl$_4$ solution (237.44 g of TiCl$_4$+207.76 g of H$_2$O) are subsequently metered in at pH 2.1. During the addition of the TiCl$_4$ solution, the pH is in each case kept constant using NaOH solution (32%). For work-up, the pigment is filtered off, washed with deionised water, dried at 110° C. and reduced for 45 minutes at 575° C. in a forming gas atmosphere (92% of N$_2$/8% of H$_2$ or 96% of N$_2$/4% of H$_2$).

A bright pigment having a green interference colour combined with a black absorption colour is obtained.

The Lab values are measured using a Minolta CR-300 chroma meter.

| | |
|---|---|
| L value: | between 66 and 70 |
| a value: | between −21 and −17 |
| b value: | between 13 and 17 |
| C value (chroma): | between 23 and 25 |
| h° value (hue angle): | between 139 and 142 |

A commercially available Iriodin® Majestic Green interference pigment (Cr$_2$O$_3$-coated mica pigment from Merck KGaA) exhibits, by comparison, the following Lab values:

| | |
|---|---|
| L value: | about 68 |
| a value: | about −21 |
| b value: | about 12 |
| C value (chroma): | about 24 |
| h° value (hue angle): | about 149° |

By contrast, the pigment from Example 1 is distinguished, in particular, by the freedom from chromium with the same or a similar hue.

Example 2

Mica+Fe$_2$O$_3$+TiO$_2$+SiO$_2$+TiO$_2$ 100 g of mica having a particle size of 10–60 μm are suspended in 1.9 l of deionised water and heated to 80° C. with vigorous stirring. The pH of the mica suspension is set to 2.8 using 10% hydrochloric acid. 111.91 g of FeCl$_3$ solution (37.30 g of FeCl$_3$+74.61 g of H$_2$O) are subsequently metered in, during which the pH is kept constant by means of 32% sodium hydroxide solution. The suspension is subsequently stirred for 15 minutes. 890.40 g of TiCl$_4$ solution (474.88 g of TiCl$_4$+415.52 g of H$_2$O) are metered into this suspension at pH=2.1. The pH is then set to 7.0 using sodium hydroxide solution (32%), and 188.89 g of sodium water-glass solution (62.96 g of sodium water-glass (w$_{SiO2}$=27%)+125.93 g of H$_2$O) are metered in at this pH. During this addition, the pH is kept constant using hydrochloric acid (10%). 445.2 g of TiCl$_4$ solution (237.44 g of TiCl$_4$+207.76 g of H$_2$O) are subsequently metered in at pH 2.1. During the addition of the TiCl$_4$ solution, the pH is in each case kept constant using NaOH solution (32%). For work-up, the pigment is filtered off, washed with deionised water, dried at 110° C. and ignited for 0.5 hour at 600° C. under a normal atmosphere, giving a pigment having a green-yellow body colour/absorption colour.

The Lab values are measured using a Minolta CR-300 chroma meter.

| | |
|---|---|
| L value: | between 75 and 78 |
| a value: | between −3.5 and −1.5 |
| b value: | between 29 and 31 |
| C value (chroma): | between 29 and 31 |
| h° value (hue angle): | between 93° and 97° |

Example 3

Mica+Fe$_2$O$_3$+TiO$_2$+SiO$_2$+TiO$_2$ 50 g of mica having a particle size of 10–60 μm and 50 g of mica having a particle size of 5–20 μm are suspended in 1.9 l of deionised water and heated to 80° C. with vigorous stirring. The pH of the mica suspension is set to 2.8 using 10% hydrochloric acid. 42 g of FeCl$_3$ solution (14 g of FeCl$_3$+28 g of H$_2$O) are subsequently metered in, during which the pH is kept constant by means of 32% sodium hydroxide solution. The suspension is subsequently stirred for 15 minutes. 408.1 g of TiCl$_4$ solution (217.6 g of TiCl$_4$+190.5 g of H$_2$O) are metered into this suspension at pH=2.1. The pH is then set to 7.0 using sodium hydroxide solution (32%), and 611.1 g of sodium water-glass solution (203.7 g of sodium water-glass (w$_{SiO2}$=27%)+407.4 g of H$_2$O) are metered in at this pH. During this addition, the pH is kept constant using hydrochloric acid (10%). 200.4 g of TiCl$_4$ solution (106.9 g of TiCl$_4$+93.5 g of H$_2$O) are subsequently metered in at pH 2.1. During the addition of the TiCl₄ solution, the pH is in each case kept constant using NaOH solution (32%). For work-up, the pigment is filtered off, washed with deionised water, dried at 110° C. and ignited for 0.5 hour at 600° C. under a normal atmosphere, giving a pigment having a golden body colour/absorption colour.

The Lab values are measured using a Minolta CR-300 chroma meter.

| L value: | between 80 and 84 |
| a value: | between 2 and 6 |
| b value: | between 38 and 40 |
| C value (chroma): | between 38 and 40 |
| h° value (hue angle): | between 81° and 87° |

Example 4

Mica+Fe₃O₄+TiO₂+SiO₂+TiO₂

50 g of mica having a particle size of 10–130 μm and 50 g of mica having a particle size of 5–20 μm are suspended in 1.9 l of deionised water and heated to 80° C. with vigorous stirring. The pH of the mica suspension is set to 2.8 using 10% hydrochloric acid. 97.9 g of FeCl₃ solution (32.6 g of FeCl₃+65.3 g of H₂O) are subsequently metered in, during which the pH is kept constant by means of 32% sodium hydroxide solution. The suspension is subsequently stirred for 15 minutes. 742 g of TiCl₄ solution (395.7 g of TiCl₄+346.3 g of H₂O) are metered into this suspension at pH=2.1. The pH is then set to 7.0 using sodium hydroxide solution (32%), and 333.3 g of sodium water-glass solution (111.1 g of sodium water-glass (w_{SiO2}=27%)+222.2 g of H₂O) are metered in at this pH. During this addition, the pH is kept constant using hydrochloric acid (10%). 371 g of TiCl₄ solution (197.9 g of TiCl₄+173.1 g of H₂O) are subsequently metered in at pH 2.1. During the addition of the TiCl₄ solution, the pH is in each case kept constant using NaOH solution (32%). For work-up, the pigment is filtered off, washed with deionised water, dried at 110° C. and reduced for 45 minutes at 575° C. in a forming gas atmosphere (92% of N₂/8% of H₂ or 96% of N₂/4% of H₂), giving a pigment having a dark-blue body colour.

The Lab values are measured using a Minolta CR-300 chroma meter.

| L value: | between 52 and 56 |
| a value: | between −3 and 0 |
| b value: | between −20 and −16 |
| C value (chroma): | between 20 and 16 |
| h° value (hue angle): | between 259° and 270° |

Use Examples

Example A

Nail Varnish

| 2.00% | of pigment from Example 1 (1) |
| 98.00% | of thixotropic nail-varnish base 1348 (Toluene, Ethyl Acetate, Butyl Acetate, Nitrocellulose, Tosylamide/For- |

-continued

| | maldehyde, Resin, Dibutyl Phthalate, Isopropyl Alcohol, Stearalkonium Hectorite, Camphor, Acrylate Copolymer, Benzophenone-1) (2) |

Sources of Supply:
(1) Merck KGaA
(2) International Lacquers S. A.

Example B

Eye Shadow

| Phase A | |
| 30.00% | of pigment from Example 1 (1) |
| 49.50% | of Talc (1) |
| 7.50% | of Potato Starch (Solanum Tuberosum) (2) |
| 2.50% | of Magnesium Stearate (1) |
| Phase B | |
| 9.14% | of Isopropyl Stearate (3) |
| 0.53% | of Cetyl Palmitate (1) |
| 0.53% | of Ewalin 1751 (Petrolatum) (4) |
| 0.20% | of Fragrance Elegance #79228 D MF (perfume) (5) |
| 0.10% | of Propyl 4-Hydroxybenzoate (Propylparaben) (1) |

The constituents of phase A are mixed homogeneously. The molten phase B is subsequently added to the powder mixture with stirring. The powders are pressed at 40–50 bar.
Sources of Supply:
(1) Merck KGaA
(2) Südstärke GmbH
(3) Cognis GmbH
(4) H. Erhard Wagner GmbH
(5) Haarmann & Reimer GmbH

Example C

Lipstick

| Phase A | |
| 15.00% | of pigment from Example 2 (1) |
| Phase B | |
| 8.75% | of Beeswax White (Cera Alba) (1) |
| 5.25% | of Paracera C 44 (Copernicia Cerifera (Carnauba Wax, Ceresin) (2) |
| 3.50% | of Adeps Lanae (Lanolin) (3) |
| 5.60% | of Isopropyl Myristate (4) |
| 2.10% | of Paraffin Viscous (Paraffinum Liquidum (Mineral Oil) (1) |
| 0.05% | of OXYNEX ® K liquid (PEG-8, Tocopherol, Ascorbyl Palmitate, Ascorbic Acid, Citric Acid) (1) |
| 0.10% | of Propyl 4-Hydroxybenzoate (Propylparaben) (1) |
| 59.45% | of Castor Oil (Ricinus Communis) (3) |
| Phase C | |
| 0.20% | of Fragrance Tendresse #75418C (perfume) (5) |

The constituents of phase B are heated to 75° C. and melted. The pigments of phase A are added, and everything is stirred well. The lipstick material is then stirred for 15 minutes with the perfume from phase C in the casting apparatus heated to 65° C. The homogeneous melt is poured into the casting moulds pre-heated to 55° C. The moulds are subsequently cooled, and the cold castings are removed.

Sources of Supply:
(1) Merck KGaA
(2) Paramelt
(3) Henry Lamotte GmbH
(4) Cognis GmbH
(5) Haarmann & Reimer GmbH Example D Clear Shower Gel

| Phase A | |
|---|---|
| 0.10% | of pigment from Example 1 (1) |
| 0.76% | of Keltrol T (Xanthan Gum) (2) |
| 65.15% | of water (Aqua) |
| Phase B | |
| 20.00% | of Plantacare 2000 UP (Decyl Glucoside) (3) |
| 3.60% | of Texapon ASV (Magnesium Oleth Sulfate, Sodium Oleth Sulfate, Magnesium Laureth-8 Sulfate, Sodium Laureth-8 Sulfate, Magnesium Laureth Sulfate, Sodium Laureth Sulfate) (3) |
| 0.20% | of Brondidox L (Propylene Glycol, 5-Bromo-5-Nitro-1,3-Dioxane) (3) |
| 0.05% | of Fragrance Everest 79658 SB (perfume) (4) |
| q.s. % | of Dye stuff solution |
| Phase C | |
| 0.15% | of Citric Acid Monohydrate (Citric acid) (1) |
| 10.00% | of water, demineralised (Aqua) |

The pigment is dispersed in the water of phase A. Addition of Keltrol T and careful mixing of the constituents. Phase B and phase C are added to phase A with stirring. The mixture is stirred slowly until the homogeneous gel has formed. The pH is set to 6.0–6.5.

Sources of Supply:
(1) Merck KGaA
(2) Kelco
(3) Cognis GmbH
(4) Haarmann & Reimer GmbH Example E Eye Shadow Gel

| Phase A | |
|---|---|
| 20.00% | of pigment from Example 2 (1) |
| 3.00% | of Ronasphere ® (Silica) (1) |
| 0.30% | of Carbopol ETD 2001 (Carbomer) (2) |
| q.s. % | of Citric Acid Monohydrate (Citric Acid) (1) |
| 60.00% | of water, demineralised (Aqua) |
| Phase B | |
| 2.00% | of Glycerol, Anhydrous (Glycerin) (1) |
| 1.00% | of Germaben II (Propylene Glycol, Diazolidinyl Urea, Methylparaben, Propylparaben) (3) |
| 0.70% | of Triethanolamine (Trithanolamine) (1) |
| 13.00% | of water, demineralised (Aqua) |

The constituents of phase A are mixed. Addition of a few drops of citric acid in order to reduce the viscosity and addition of carbomer with stirring. Stirring until everything has dispersed. Dissolution of the constituents of phase B and stirring until a homogeneous solution has formed. Addition of phase B to phase A with stirring, and adjustment of the pH to 7.7–7.5.

Sources of Supply:
(1) Merck KGaA/Rona®
(2) B F Goodrich GmbH
(3) ISP Global Technologies Example E Mascara

| Phase A | |
|---|---|
| 15.00% | of pigment from Example 4 (1) |
| Phase B | |
| 8.00% | of Stearic Acid (Stearic Acid) (1) |
| 6.00% | of Beeswax white (Cera Alba) (1) |
| 4.00% | of Carnauba Wax 2442 L (Copernicia Cerifera) (2) |
| 3.00% | of Eutanol G (Octyldodecanol) (3) |
| 2.00% | of Arlacel 83 (Sorbitan Sesquioleate) (4) |
| 0.10% | of Propyl 4-Hydroxybenzoate (Propylparaben) (1) |
| 0.50% | of RonaCare ™ Tocopherol Acetate (Tocopheryl Acetate) (1) |
| Phase C | |
| 2.30% | of Triethanolamine (1) |
| 8.00% | of Water Soluble Shellac SSB 63 (Shellac) (5) |
| 0.25% | of Methyl 4-Hydroxybenzoate (Methylparaben) (1) |
| 0.01% | of RonaCare ™ Biotin (Biotin) (1) |
| 50.84% | of water, demineralised (Aqua) |

The constituents of phase B are heated to 80° C. and melted with stirring. Shellac of phase C is mixed with water, heated to 75° C. and dissolved in the other constituents of phase C. Phase C is added to the mixture of phase A and phase B at 75° C. and homogenised for 2 minutes. The mascara is cooled to room temperature and adjusted to pH 7.0–7.5.

Sources of Supply:
(1) Merck KGaA/Rona®
(2) Kahl & Co.
(3) Cognis GmbH
(4) Uniqema
(5) Paroxite Ltd.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A coloured interference pigment comprising platelet-shaped substrates having:

(A) a coloured coating having a refractive index of n>1.8, (B) a colourless coating having a refractive index of n>1.8, (C) a colourless coating having a refractive index of n≦1.8, (D) a colourless coating having a refractive index of n>1.8, and optionally (E) an outer protective layer, wherein coating (A) is on top of said substrate, coating (B) is between coating (A) and coating (C), and, if layer (B) is present, coating (D) is between coating (C) and layer (E).

2. A coloured interference pigment according to claim 1, wherein said platelet-shaped substrates have an outer protective layer (E).

3. A coloured interference pigment according to claim 1, wherein said platelet-shaped substrates are natural or synthetic mica, BiOCl, glass platelets, $Al_2O_3$ platelets, $SiO_2$ platelets or $TiO_2$ platelets, or mixtures thereof.

4. A coloured interference pigment according to claim 1, wherein layer (A) contains $Fe_2O_3$, $Fe_3O_4$, $Ce_2O_3$, $Cr_2O_3$, Ti sub-oxides, titanium oxynitrides, titanium nitride, molybdenum oxides, CoO, $Co_3O_4$, $VO_2$, $V_2O_3$, NiO, $MoS_2$, $WS_2$, $V_2O_5$, CuO, $Cu_2O$, $Ag_2O$, $CeO_2$, $MnO_2$, $Mn_2O_3$, $Mn_2O_5$ or mixtures thereof (mixed oxides).

5. A coloured interference pigment according to claim 3, wherein layer (A) contains $Fe_2O_3$, $Fe_3O_4$, $Ce_2O_3$, $Cr_2O_3$, Ti sub-oxides, titanium oxynitrides, titanium nitride, molybdenum oxides, CoO, $Co_3O_4$, $VO_2$, $V_2O_3$, NiO, $MoS_2$, $WS_2$, $V_2O_5$, CuO, $Cu_2O$, $Ag_2O$, $CeO_2$, $MnO_2$, $Mn_2O_3$, $Mn_2O_5$ or mixtures thereof (mixed oxides).

6. A coloured interference pigment according to claim 1, wherein layer (B) contains $TiO_2$, $ZrO_2$, ZnO, BiOCl or mixtures thereof.

7. A coloured interference pigment according to claim 3, wherein layer (B) contains $TiO_2$, $ZrO_2$, ZnO, BiOCl or mixtures thereof.

8. A coloured interference pigment according to claim 4, wherein layer (B) contains $TiO_2$, $ZrO_2$, ZnO, BiOCl or mixtures thereof.

9. A coloured interference pigment according to claim 5, wherein layer (B) contains $TiO_2$, $ZrO_2$, ZnO, BiOCl or mixtures thereof.

10. A coloured interference pigments according to claim 1, wherein layer (C) contains $SiO_2$, $MgF_2$, $Al_2O_3$ or mixtures thereof.

11. A coloured interference pigments according to claim 9, wherein layer (C) contains $SiO_2$, $MgF_2$, $Al_2O_3$ or mixtures thereof.

12. A coloured interference pigment according to claim 1, wherein layer (D) contains $TiO_2$, $ZrO_2$, ZnO, BiOCl or mixtures thereof.

13. A coloured interference pigment according to claim 10, wherein layer (D) contains $TiO_2$, $ZrO_2$, ZnO, BiOCl or mixtures thereof.

14. A coloured interference pigment according to claim 1, wherein layer (B) and layer (D) have the same composition.

15. A coloured interference pigment according to claim 14, wherein layer (B) and layer (D) are $TiO_2$ layers.

16. A process for the preparation of a coloured pigment according to claim 1, comprising: coating the platelet-shaped substrates by wet-chemical methods, by hydrolytic decomposition of metal salts in aqueous medium, by CVD methods or by PVD methods.

17. In paints, surface coatings, printing inks, plastics, ceramic materials, glasses, in cosmetic formulations, coatings for laser marking, pigment preparations, and dry preparations, the improvement wherein coloured interference pigment according to claim 1 is contained therein.

18. A pigment preparation comprising one or more binders, optionally one or more additives and one or more coloured interference pigments according to claim 1.

19. In a dry preparations, such as pellets, granules, chips, and briquettes, the improvement wherein said preparation comprises at least one coloured interference pigments according to claim 1.

20. A coloured interference pigment according to claim 1, wherein said substrates are selected from natural or synthetic mica, talc, kaolin, platelet-shaped iron oxides or aluminium oxides, BiOCl, glass platelets, $SiO_2$ platelets, $TiO_2$ platelets, and graphite platelets.

21. A coloured interference pigment according to claim 1, wherein said substrates are a mixture of: mica platelets and $SiO_2$ platelets; mica platelets and $Al_2O_3$ platelets; mica platelets and glass platelets; mica platelets and $TiO_2$ platelets mica platelets and oxynitride platelets; mica platelets and nitride platelets; mica platelets and pearl essence; mica platelets and graphite platelets; mica platelets and BiOCl; $SiO_2$ platelets and $Al_2O_3$ platelets; or glass platelets and $SiO_2$ platelets.

22. A coloured interference pigment according to claim 1, wherein the platelet-shaped substrates have a thickness of 0.05–1.5 μm, a width of 1 to 250 μm, and a length of 1 to 250 μm.

23. A coloured interference pigment according to claim 1, wherein the platelet-shaped substrates are N mica having a thickness of 0.05–1.5 μm, a width of 10–60 μm, and a length of 10–60 μm and F mica having a thickness of 0.05–1.5 μm, a width of 5–20 μm, and a length of 5–20 μm; N mica having a thickness of 0.05–1.5 μm, a width of 10–130 μm, and a length of 10–130 μm and S mica having a thickness of 0.05–1.5 μm, a width of 10–130 μm, and a length of 10–130 μm; or F mica having a thickness of 0.05–1.5 μm, a width of 5–130 μm, and a length of 5–130 μm and S mica having a thickness of 0.05–1.5 μm, a width of 5–130 μm, and a length of 5–130 μm.

24. A coloured interference pigment according to claim 1, wherein layers (B) and (D) each have a refractive index of $n \geq 2.0$.

25. A coloured interference pigment according to claim 1, wherein the thickness of layer (A) is 1 to 100 nm, the thickness of layers (B) and (D) are each 20 to 250 nm, and the thickness of layer (C) is 20 to 200 nm.

26. A coloured interference pigment according to claim 1, wherein the pigment is selected from the following:

substrate+$Fe_2O_3$ (A)+$TiO_2$ (B)+$SiO_2$ (C)+$TiO_2$ (D);
substrate+$Fe_3O_4$ (A)+$TiO_2$ (B)+$SiO_2$ (C)+$TiO_2$ (D);
substrate+$Fe_2O_3$ (A)+$TiO_2$ (B)+$Al_2O_3$ (C)+$TiO_2$ (D);
substrate+$Fe_3O_4$ (A)+$TiO_2$ (B)+$Al_2O_3$ (C)+$TiO_2$ (D);
substrate+$V_2O_5$ (A)+$TiO_2$ (B)+$SiO_2$ (C)+$TiO_2$ (D);
substrate+$MnO_2$ (A)+$TiO_2$ (B)+$SiO_2$ (C)+$TiO_2$ (D);
substrate+$MnO_2$ (A)+$TiO_2$ (B)+$Al_2O_3$ (C)+$TiO_2$ (D);
substrate+$Ag_2O$ (A)+$TiO_2$ (B)+$SiO_2$ (C)+$TiO_2$ (D);
substrate+$Ag_2O$ (A)+$TiO_2$ (B)+$Al_2O_3$ (C)+$TiO_2$ (D);
substrate+CoO (A)+$TiO_2$ (B)+$SiO_2$ (C)+$TiO_2$ (D);
substrate+$Cr_2O_3$ (A)+$TiO_2$ (B)+$SiO_2$ (C)+$TiO_2$ (D);
substrate+$Cr_2O_3$ (A)+$TiO_2$ (B)+$Al_2O_3$ (C)+$TiO_2$ (D);
substrate+Ti suboxides (A)+$TiO_2$ (B)+$SiO_2$ (C)+$TiO_2$ (D);
substrate+Ti suboxides (A)+$TiO_2$ (B)+$Al_2O_3$ (C)+$TiO_2$ (D);
substrate+$Fe_2O_3$ (A)+$ZrO_2$ (B)+$SiO_2$ (C)+$ZrO_2$ (D);
substrate+$Fe_2O_3$ (A)+ZnO (B)+$SiO_2$ (C)+$ZrO_2$ (D);
substrate+$Fe_3O_4$ (A)+$ZrO_2$ (B)+$SiO_2$ (C)+$ZrO_2$ (D);
substrate+$Fe_3O_4$ (A)+$ZrO_2$ (B)+$SiO_2$ (C)+$TiO_2$ (D); and
substrate+$Fe_2O_3$ (A)+$TiO_2$ (B)+$SiO_2$ (C)+$ZrO_2$ (D).

27. A coloured interference pigment comprising platelet-shaped substrates having:

(A) a coloured coating having a refractive index of n>1.8, (B) a colourless coating having a refractive index of n>1.8, (C) a colourless coating having a refractive index of $n \leq 1.8$, (D) a colourless coating having a refractive index of n>1.8, and optionally (E) an outer protective layer, wherein the pigment is selected from the following:
- substrate+$Fe_2O_3$ (A)+$TiO_2$ (B)+$SiO_2$ (C)+$TiO_2$ (D);
- substrate+$Fe_3O_4$ (A)+$TiO_2$ (B)+$SiO_2$ (C)+$TiO_2$ (D);
- substrate+$Fe_2O_3$ (A)+$TiO_2$ (B)+$Al_2O_3$ (C)+$TiO_2$ (D);
- substrate+$Fe_3O_4$ (A)+$TiO_2$ (B)+$Al_2O_3$ (C)+$TiO_2$ (D);
- substrate+$V_2O_5$ (A)+$TiO_2$ (B)+$SiO_2$ (C)+$TiO_2$ (D);
- substrate+$MnO_2$ (A)+$TiO_2$ (B)+$SiO_2$ (C)+$TiO_2$ (D);
- substrate+$MnO_2$ (A)+$TiO_2$ (B)+$Al_2O_3$ (C)+$TiO_2$ (D);
- substrate+$Ag_2O$ (A)+$TiO_2$ (B)+$SiO_2$ (C)+$TiO_2$ (D);
- substrate+$Ag_2O$ (A)+$TiO_2$ (B)+$Al_2O_3$ (C)+$TiO_2$ (D);
- substrate+CoO (A)+$TiO_2$ (B)+$SiO_2$ (C)+$TiO_2$ (D);
- substrate+$Cr_2O_3$ (A)+$TiO_2$ (B)+$SiO_2$ (C)+$TiO_2$ (D);
- substrate+$Cr_2O_3$ (A)+$TiO_2$ (B)+$Al_2O_3$ (C)+$TiO_2$ (D);
- substrate+Ti suboxides (A)+$TiO_2$ (B)+$SiO_2$ (C)+$TiO_2$ (D);
- substrate+Ti suboxides (A)+$TiO_2$ (B)+$Al_2O_3$ (C)+$TiO_2$ (D);
- substrate+$Fe_2O_3$ (A)+$ZrO_2$ (B)+$SiO_2$ (C)+$ZrO_2$ (D);
- substrate+$Fe_2O_3$ (A)+ZnO (B)+$SiO_2$ (C)+$ZrO_2$ (D);
- substrate+$Fe_3O_4$ (A)+$ZrO_2$ (B)+$SiO_2$ (C)+$ZrO_2$ (D);
- substrate+$Fe_3O_4$ (A)+$ZrO_2$ (B)+$SiO_2$ (C)+$TiO_2$ (D); and
- substrate+$Fe_2O_3$ (A)+$TiO_2$ (B)+$SiO_2$ (C)+$ZrO_2$ (D), and in each case is optionally provided an outer protective layer (E).

28. A coloured interference pigment according to claim 1, wherein coating (B) is on top of coating (A).

29. A coloured interference pigment according to claim 1, wherein coating (C) is on top of coating (B).

30. A coloured interference pigment according to claim 28, wherein coating (C) is on top of coating (B).

31. A coloured interference pigment according to claim 1, wherein coating (D) is on top of coating (C).

32. A coloured interference pigment according to claim 1, wherein said pigment comprises protective layer (E) and said protective layer (E) is on top of coating (D).

33. A coloured interference pigment according to claim 1, wherein coating (A) is on top of said substrate, coating (B) is on top of coating (A), coating (C) is on top of coating (B), and coating (D) is on top of coating (C).

34. A coloured interference pigment according to claim 1, wherein the platelet-shaped substrates are selected from: mica having a thickness of 0.05–1.5 μm, a width of 10–60 μm, and a length of 10–60 μm, and mica having a thickness of 0.05–1.5 μm, a width of 5–20 μm, and a length of 5–20 μm; mica having a thickness of 0.05–1.5 μm, a width of 10–130 μm, and a length of 10–130 μm, and mica having a thickness of 0.05–1.5 μm, a width of 10–130 μm, and a length of 10–130 μm; and mica having a thickness of 0.05–1.5 μm, a width of 5–130 μm, and a length of 5–130 μm, and mica having a thickness of 0.05–1.5 μm, a width of 5–130 μm, and a length of 5–130 μm.

* * * * *

UNITED STATES PATENT AND TRADEMARK OFFICE
CERTIFICATE OF CORRECTION

PATENT NO.    : 6,719,838 B2
DATED         : April 13, 2004
INVENTOR(S)   : Lillia Heider et al.

It is certified that error appears in the above-identified patent and that said Letters Patent is hereby corrected as shown below:

<u>Column 10,</u>
Line 63, reads "(B)" should read -- (E) --

Signed and Sealed this

Twenty-first Day of December, 2004

JON W. DUDAS
*Director of the United States Patent and Trademark Office*